United States Patent
Jabs et al.

(10) Patent No.: US 8,210,031 B2
(45) Date of Patent: Jul. 3, 2012

(54) DEVICE AND METHOD FOR THE DETERMINATION OF AN ANALYTE IN A SAMPLE OF LIQUID

(75) Inventors: Holger Jabs, Gorxheimertal (DE); Norbert Ladiges, Bruehl (DE); Herbert Fink, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 414 days.

(21) Appl. No.: 12/560,518

(22) Filed: Sep. 16, 2009

(65) Prior Publication Data

US 2010/0107743 A1    May 6, 2010

(30) Foreign Application Priority Data

Sep. 17, 2008 (EP) .................... 08016360

(51) Int. Cl.
  *G01N 1/00* (2006.01)
  *G01N 33/49* (2006.01)
(52) U.S. Cl. ........................... 73/61.59
(58) Field of Classification Search ............ 73/61.59
  See application file for complete search history.

(56) References Cited

U.S. PATENT DOCUMENTS

| | | | | |
|---|---|---|---|---|
| 4,803,154 A | * | 2/1989 | Uo et al. | 435/7.93 |
| 6,265,016 B1 | * | 7/2001 | Hostettler et al. | 427/2.11 |
| 6,830,934 B1 | * | 12/2004 | Harding et al. | 436/166 |
| 7,025,774 B2 | * | 4/2006 | Freeman et al. | 606/181 |
| 2006/0079810 A1 | * | 4/2006 | Patel et al. | 600/583 |
| 2008/0060424 A1 | * | 3/2008 | Babic et al. | 73/61.41 |
| 2009/0043227 A1 | * | 2/2009 | Fujiwara et al. | 600/583 |
| 2009/0198119 A1 | * | 8/2009 | Niederberger et al. | 600/365 |
| 2010/0084268 A1 | * | 4/2010 | Pierce et al. | 204/403.14 |

FOREIGN PATENT DOCUMENTS

| | | |
|---|---|---|
| EP | 1 156 325 A1 | 1/2000 |
| EP | 1 916 309 A2 | 10/2007 |
| WO | 99/30152 | 6/1999 |

OTHER PUBLICATIONS

Masahide Gunji, et al., "Local In-Situ Hydrophilic Treatment of Micro-Channels Using Surface Discharge", The 13th International Conference on Solid-State Sensors, Actuators and Microsystems, Seoul, Korea, Jun. 5-9, 2005, pp. 1187-1190.

* cited by examiner

*Primary Examiner* — John Fitzgerald
(74) *Attorney, Agent, or Firm* — Dinsmore & Shohl LLP

(57) ABSTRACT

A device for determining an analyte in a sample of liquid comprises an analysis apparatus configured to analyze a sample of liquid applied to an analytical area of a test element. The device comprises further an apparatus configured to prepare a surface of the analytical area by conferring hydrophilic properties to the surface. Analytes in test samples are determined by methods employing the device.

13 Claims, 1 Drawing Sheet

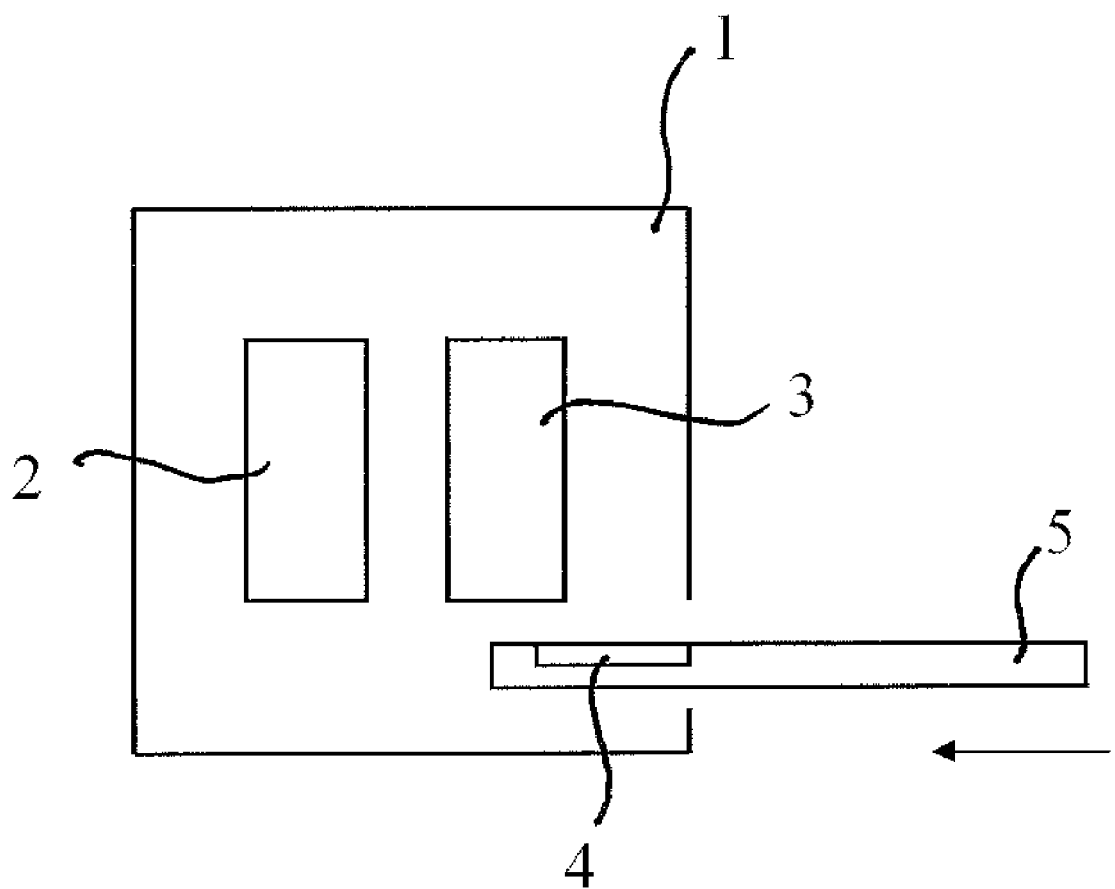

DEVICE AND METHOD FOR THE DETERMINATION OF AN ANALYTE IN A SAMPLE OF LIQUID

CROSS-REFERENCE TO RELATED APPLICATIONS

This application claims the benefit of priority under 35 U.S.C. §119 of European Application No. 08 016 360.3, filed Sep. 17, 2008.

TECHNICAL FIELD

The invention relates to analytical devices and, in particular, to devices and methods for determining one or more analytes in a sample of liquid.

BACKGROUND

Analytical devices and methods may be used to determine one or more analytes in samples of liquid. The liquid may comprise, for example, bodily fluids including, but not limited to, blood. The devices may be stationary, as in a laboratory instrument, or portable, as in a hand-held instrument.

Patient tests, such as those used in the care and treatment of diabetic patients, frequently employ disposable test elements for determining analytes in samples of bodily fluids, for example. Example disposable test elements include test strips. These test elements typically include a suitable analytical area that has been prepared on the test element. The determination of the analyte or analytes in the bodily fluid or some other sample of liquid is conducted by applying the sample of liquid to the analytical area of the test element where, normally, one or more test reactions occur. Following the application of the sample, the test element is evaluated using a testing or analytical instrument such as, for example, a hand-held instrument. The evaluation may involve, for example, an optical measurement, an electronic measurement, or both.

In some applications, optimal determination of the analyte in the liquid may require a surface within the analytical area to have hydrophilic properties that cause the liquid sample material to spread out easily. One method for forming a hydrophilic surface includes coating the analytical area with a hydrophilic material. Such a method has the drawbacks of a limited number of suitable materials and of tendencies for the hydrophilic material to influence the functionality of the test element. Because functional coatings must be chosen to satisfy very specific criteria, they are subject of extensive development activity that is time-consuming and expensive. Moreover, the application of the coating and the process control measures during production of the coatings also are prohibitively expensive. Though coatings can provide an effective hydrophilic surface within the analytical area of the test element, the coatings also limit the durability and the mechanical strength of the test element. Therefore, there remains an ongoing need for alternative methods and devices for forming hydrophilic surfaces on analytical areas of test elements.

SUMMARY

Disclosed are devices and methods for determining an analyte in a sample of liquid, wherein a hydrophilic surface can be formed on a test element for in a simple and reliable manner.

In one embodiment a device for the determination of an analyte in a sample of liquid comprises an analysis apparatus. The analysis apparatus is configured to analyze a sample of liquid after the sample is applied to an analytical area of a test element prepared for an analysis of the sample of liquid. The device further comprises a hydrophilization apparatus. The hydrophilization apparatus is configured to confer hydrophilic properties to a surface in the analytical area during the preparation of the test element.

In another embodiment, a method for the determination of an analyte in a sample of liquid with the aid of an analytical instrument comprises providing a sample of liquid and a test element, the test element comprising an analytical area. A surface of the analytical area is treated with a hydrophilization apparatus to form a treated analytical area. The sample of liquid is applied to the treated analytical area. The test element is introduced into the analytical instrument either before or after the surface of the analytical area is treated with the hydrophilization apparatus. The sample of liquid is analyzed with an analytical apparatus incorporated into the analytical instrument.

Further embodiments of the device and method will become apparent through the detailed description and drawing contained herein.

BRIEF DESCRIPTION OF THE DRAWING

Though the specification concludes with claims particularly pointing out and distinctly claiming the invention, it is believed that the present invention will be better understood from the following description taken in conjunction with the accompanying drawings, in which:

FIG. 1 shows a schematic representation of an embodiment of analytical instrument comprising an analytical apparatus and a hydrophilization apparatus.

DETAILED DESCRIPTION

Features and advantages of the invention will now be described with occasional reference to specific embodiments. However, the invention may be embodied in different forms and should not be construed as limited to the embodiments set forth herein. Rather, these embodiments are provided so that this disclosure will be thorough and complete and will fully convey the scope of the invention to those skilled in the art.

Shown in FIG. 1 is a schematic representation of an analytical instrument 1 with an analytical apparatus 2 and a hydrophilization apparatus 3. The analytical apparatus 2 is configured to analyze a sample of a liquid to be determined with the aid of a measuring or analytical technique selected to suit the particular application. The liquid is applied to an analytical area 4 of a test element 5. For example, the analytical apparatus 2 may comprise an optical measurement apparatus, with which a measurement light can be directed toward the analytical area 4. This enables evaluation of, for example, fluorescent or absorption properties of the liquid under determination. Depending on the particular application, the analytical apparatus 2 can use one or more different measurement principles to determine the characteristics of the sample of liquid.

To ensure that the liquid sample spreads well over the analytical area 4, the surface of the analytical area 4 is provided with hydrophilic properties (hydrophilized). The hydrophilization apparatus 3 is provided for this purpose. In example embodiments, the hydrophilization apparatus 3 may comprise a plasma-treatment apparatus. Such a plasma-treatment apparatus may comprise a plasma-generating component to form a plasma. The plasma may be used to treat a surface in the analytical area 4 and thereby hydrophilize the surface. In one example embodiment, the plasma treatment occurs after the test element 5 has been inserted into the analytical instrument 1. In another example embodiment, the plasma treatment can be carried out using a gas mixture that optionally contains one or more oxidizing substances such as, for example, ozone.

Plasma may be described as an at least partially ionized gas that contains free charge-carriers such as ions or electrons. A plasma is generated by the input of energy from an external source. If the coupling of energy does not take place, the plasma disappears because the positive and negative charge carriers recombine to form neutral atoms, molecules, or radicals. Furthermore, the charge carriers can be lost by ambipolar diffusion, such as to electrically conducting walls or into the vacuum of space. In addition to this, account must be taken of thermal radiation losses of the plasma. To compensate for the permanent loss of ionized particles, the ionized particles must be continually regenerated. The regeneration may occur, for example, by acceleration and impact ionization.

A plasma can be generated in a variety of ways involving the input of energy. These include without limitation: thermal excitation, chemical and nuclear reactions, radiation excitation, laser beam excitation, electrostatic field excitation, excitation by direct current, excitation by electromagnetic fields, capacitive electric excitation, excitation by exploding wires, inductive (magnetic) excitation, excitation by microwave radiation, and by the pinch-effect.

Plasma-generating components are available in various forms. Plasma-generating components may be miniaturized components or components of microsystems. Example components include, but are not limited to, microwave plasma generators that use microwave technology to generate the plasma and microplasma reactors. However, it will be understood that other designs can be used as plasma-generating components, depending on the applications.

In further embodiments, the plasma-treatment apparatus may comprise a microplasma reactor. Microplasma reactors may possesses a core comprising comb-shaped, micro-structured electrodes which engage each other. Microplasma reactors may be formed, for example, using photolithography. The use of very narrow gap widths makes possible the production of a homogenous plasma at low ignition voltages. In example embodiments, the plasma-treatment apparatus may comprise a plurality of microplasma reactors arranged in parallel.

In some embodiments the plasma-treatment apparatus may comprise a microwave plasma generator. The plasma generated by a microwave plasma generator can be used, for example, in the 2.45-GHz Industrial, Scientific, and Medical (ISM) band. Low-pressure plasma technology makes it possible to form high-quality hydrophilic surfaces efficiently.

The hydrophilization apparatus 3 may comprise also at least one surface-treatment apparatus configured to hydrophilize the surface in the analytical area. In example embodiments, the at least one surface-treatment apparatus may be selected from the group consisting of ultrasound treatment apparatus, corona treatment apparatus, air-ionizing apparatus, ozone generators, and microwave treatment apparatus. Optionally, one or more of these surface-treatment apparatuses may be used in combination with any of the plasma-generating apparatus in the analytical apparatus 2.

In example embodiments, the surface-treatment apparatus may have a miniaturized design. As shown in the embodiment illustrated in FIG. 1, the plasma-treatment apparatus may be integrated into the analytical instrument 1. Through selection of a suitable treatment apparatus for generating a hydrophilic surface in the analytical area, the device can be adapted to suit the requirements of a variety of applications. In addition, a plurality of surface-treatment apparatuses in the device can be used, for example, to optimize the hydrophilization.

Embodiments of the device and method described above make possible the efficient and cost-effective hydrophilization of the surface of the analytical area of the test element. This allows determination of the analyte in the sample of liquid without need to coat the test element with a hydrophilic material. In some embodiments, the hydrophilization may occur during the preparation of the test element. In example embodiments, the analytical instrument comprising the analytical apparatus and the hydrophilization apparatus can be integrated in a hand-held instrument, a stationary instrument such as a laboratory instrument, or a blood-analyzing instrument that is either stationary or portable. In other embodiments the analytical apparatus and the hydrophilization apparatus may be integrated components of an analytical instrument, and optionally they may be integrated into a common housing.

The embodiments of the device and method described above enable an end user to produce a hydrophilic surface in the analytical area of the test element virtually instantaneously whenever and wherever an analysis or a measurement is needed. In example embodiments, the test element may be a test strip, such as a disposable test strip. Without the need for a hydrophilic coating over the analytical area of the test element, the production process for test elements is simplified.

What is claimed is:

1. A device for the determination of an analyte in a sample of liquid, the device comprising:
    an analytical apparatus configured to analyze a sample of liquid after the sample is applied to an analytical area of a test element prepared for an analysis of the sample of liquid; and incorporating
    a hydrophilization apparatus configured to confer hydrophilic properties to a surface in the analytical area during the preparation of the test element.

2. The device of claim 1, wherein the hydrophilization apparatus comprises a plasma-treatment apparatus configured to treat the surface in the analytical area with a plasma during hydrophilization.

3. The device of claim 1, wherein the plasma-treatment apparatus comprises a microwave plasma generator.

4. The device of claim 1, wherein the plasma-treatment apparatus comprises a microplasma reactor.

5. The device of claim 1, wherein the hydrophilization apparatus comprises a surface-treatment apparatus configured to hydrophilize the surface in the analytical area, the surface-treatment apparatus being selected from group consisting of an ultrasound treatment apparatus, a corona treatment apparatus, an air-ionizing apparatus, an ozone generator, and a microwave-treatment apparatus.

6. The device of claim 1, wherein the hydrophilization apparatus is a microapparatus.

7. A method for the determination of an analyte in a sample of liquid with the aid of an analytical instrument, the method comprising:
    providing a sample of liquid and a test element, the test element comprising an analytical area;
    treating a surface of the analytical area with a hydrophilization apparatus to form a treated analytical area;
    applying the sample of liquid to the treated analytical area;
    introducing the test element into the analytical instrument; and analyzing the sample of liquid with an analytical apparatus incorporated into the analytical instrument.

8. The method of claim 7, wherein the hydrophilization apparatus comprises a plasma-treatment apparatus.

9. The method of claim 7, wherein the treating the surface of the analytical area occurs after the introducing the test element.

10. The method of claim 7, wherein the hydrophilization apparatus comprises a microwave plasma generator.

11. The method of claim 7, wherein the hydrophilization apparatus comprises a microplasma reactor.

12. The method of claim 7, wherein the hydrophilization apparatus comprises a surface-treatment unit incorporated into the hydrophilization apparatus, the surface-treatment unit being selected from the group consisting of an ultrasound-treatment apparatus, a corona-treatment apparatus, and air-ionizing apparatus, an ozone generator, and a microwave-treatment apparatus.

13. The method claim 7, wherein the sample comprises blood.

* * * * *

UNITED STATES PATENT AND TRADEMARK OFFICE
CERTIFICATE OF CORRECTION

PATENT NO. : 8,210,031 B2  
APPLICATION NO. : 12/560518  
DATED : July 3, 2012  
INVENTOR(S) : Holger Jabs, Norbert Ladiges and Herbert Fink Page 1 of 1

It is certified that error appears in the above-identified patent and that said Letters Patent is hereby corrected as shown below:

Col. 4, Line 52, Claim 5, "from group" should read --from the group--

Signed and Sealed this
Eighteenth Day of September, 2012

David J. Kappos
*Director of the United States Patent and Trademark Office*